United States Patent
Guo et al.

(10) Patent No.: US 9,068,936 B2
(45) Date of Patent: Jun. 30, 2015

(54) GRAPHENE SENSOR

(75) Inventors: Dechao Guo, Wappingers Falls, NY (US); Shu-Jen Han, Cortlandt Manor, NY (US); Chung-Hsun Lin, White Plains, NY (US); Ning Su, Fishkill, NY (US)

(73) Assignee: International Business Machines Corporation, Armonk, NY (US)

( * ) Notice: Subject to any disclaimer, the term of this patent is extended or adjusted under 35 U.S.C. 154(b) by 11 days.

(21) Appl. No.: 13/605,107

(22) Filed: Sep. 6, 2012

(65) Prior Publication Data

US 2012/0329193 A1 Dec. 27, 2012

Related U.S. Application Data

(63) Continuation of application No. 12/727,434, filed on Mar. 19, 2010, now abandoned.

(51) Int. Cl.
| | |
|---|---|
| *H01L 29/786* | (2006.01) |
| *H01L 21/336* | (2006.01) |
| *G01N 27/414* | (2006.01) |
| *H01L 29/423* | (2006.01) |
| *H01L 29/49* | (2006.01) |
| *H01L 29/66* | (2006.01) |

(52) U.S. Cl.
CPC ...... *G01N 27/4145* (2013.01); *H01L 29/42384* (2013.01); *H01L 29/4908* (2013.01); *H01L 29/66742* (2013.01); *H01L 29/78684* (2013.01)

(58) Field of Classification Search
USPC .............. 257/24, E21.409, E29.273; 438/49; 977/734, 742, 774, 938
See application file for complete search history.

(56) References Cited

U.S. PATENT DOCUMENTS

| | | | |
|---|---|---|---|
| 7,335,395 | B2 | 2/2008 | Ward et al. |
| 7,335,528 | B2 | 2/2008 | Rueckes et al. |
| 7,563,711 | B1 | 7/2009 | Ward |
| 7,619,291 | B2 | 11/2009 | Jaiprakash |
| 2003/0157587 | A1 | 8/2003 | Gomez et al. |
| 2006/0276056 | A1 | 12/2006 | Ward |
| 2007/0014151 | A1 | 1/2007 | Zhang et al. |
| 2008/0108271 | A1 | 5/2008 | Kang et al. |
| 2008/0280038 | A1 | 11/2008 | Ward et al. |
| 2008/0283497 | A1 | 11/2008 | Gaillard et al. |
| 2008/0299307 | A1 | 12/2008 | Ward |
| 2009/0087630 | A1 | 4/2009 | Ward |
| 2009/0111282 | A1 | 4/2009 | Ward et al. |
| 2009/0140167 | A1 | 6/2009 | Ward et al. |
| 2009/0283745 | A1 * | 11/2009 | Ward et al. ......................... 257/9 |
| 2010/0025660 | A1 * | 2/2010 | Jain et al. ......................... 257/24 |

OTHER PUBLICATIONS

Caldwell, J.D. et al., "Technique for the Dry Transfer of Epitaxial Graphene onto Arbitrary Substrates," ACSNANO, vol. 4, No. 2, Jan. 25, 2010, pp. 1108-1114.

* cited by examiner

*Primary Examiner* — Lynne Gurley
*Assistant Examiner* — Vernon P Webb
(74) *Attorney, Agent, or Firm* — Cantor Colburn LLP; Vazken Alexanian

(57) ABSTRACT

A method for forming a sensor includes forming a channel in substrate, forming a sacrificial layer in the channel, forming a sensor having a first dielectric layer disposed on the substrate, a graphene layer disposed on the first dielectric layer, and a second dielectric layer disposed on the graphene layer, a source region, a drain region, and a gate region, wherein the gate region is disposed on the sacrificial layer removing the sacrificial layer from the channel.

10 Claims, 5 Drawing Sheets

GRAPHENE SENSOR

CROSS-REFERENCE TO RELATED APPLICATIONS

This is a continuation application of and claims priority from U.S. application Ser. No. 12/727,434, filed on Mar. 19, 2010, now abandoned the entire contents of which are incorporated herein by reference.

FIELD OF INVENTION

The present invention relates to sensors, and particularly graphene biosensors.

DESCRIPTION OF RELATED ART

Biosensors may be used in life sciences, clinical diagnostics, and medical research for affinity based sensing. Such as, for example, hybridization between complementary single strand DNA in microarray or affinity binding of a matched antibody-antigen pair.

Biosensors may include a biological recognition element and a transducer that converts a recognition event into a measurable electronic signal.

BRIEF SUMMARY

In one aspect of the present invention, a method for forming a sensor includes forming a channel in substrate, forming a sacrificial layer in the channel, forming a sensor having a first dielectric layer disposed on the substrate, a graphene layer disposed on the first dielectric layer, and a second dielectric layer disposed on the graphene layer, a source region, a drain region, and a gate region, wherein the gate region is disposed on the sacrificial layer removing the sacrificial layer from the channel.

In another aspect of the present invention, a method for forming a sensor includes forming a channel substrate, forming a sacrificial layer in the channel, forming a first dielectric layer on the substrate and the sacrificial layer, forming a graphene layer on the first dielectric layer, forming a second dielectric layer on the graphene layer, removing portions of the second dielectric layer and portions of the graphene layer to expose a first portion of the first dielectric layer and a second portion of the first dielectric layer, forming a source region on the exposed first portion of the first dielectric layer and drain region on the second portion of the first dielectric layer, forming a capping layer on the exposed substrate, graphene layer, source region, drain region, and second dielectric layer, removing portions of the capping layer to expose the source region, drain region, the second dielectric layer, and portions of the sacrificial layer, and removing the sacrificial layer from the channel.

Additional features and advantages are realized through the techniques of the present invention. Other embodiments and aspects of the invention are described in detail herein and are considered a part of the claimed invention. For a better understanding of the invention with the advantages and the features, refer to the description and to the drawings.

BRIEF DESCRIPTION OF THE SEVERAL VIEWS OF THE DRAWINGS

The subject matter which is regarded as the invention is particularly pointed out and distinctly claimed in the claims at the conclusion of the specification. The forgoing and other features, and advantages of the invention are apparent from the following detailed description taken in conjunction with the accompanying drawings in which:

DETAILED DESCRIPTION

Figure 1:
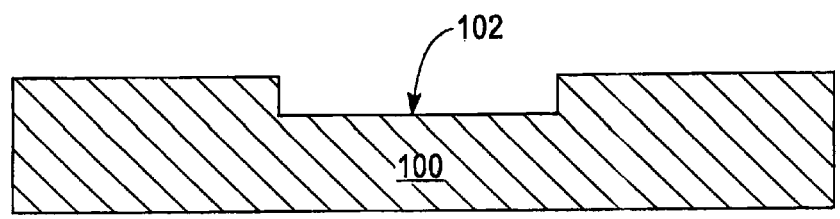
FIGS. 1-6B illustrate an exemplary method for forming a graphene sensor.

FIGS. 1-6B illustrate an exemplary method for forming a graphene sensor. FIG. 1 illustrates a side view of a channel 102 formed in a substrate 100. The substrate 100 may be, for example, a silicon substrate or a buried oxide (BOX) substrate. The channel 102 may be formed by, for example, a lithographic patterning and etching process.

Figure 2A:
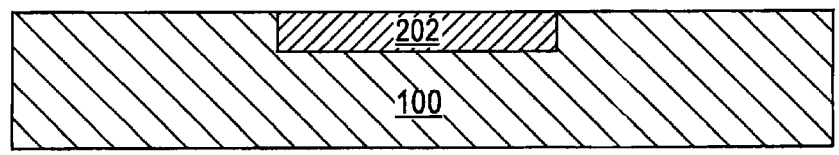
Figure 2B:
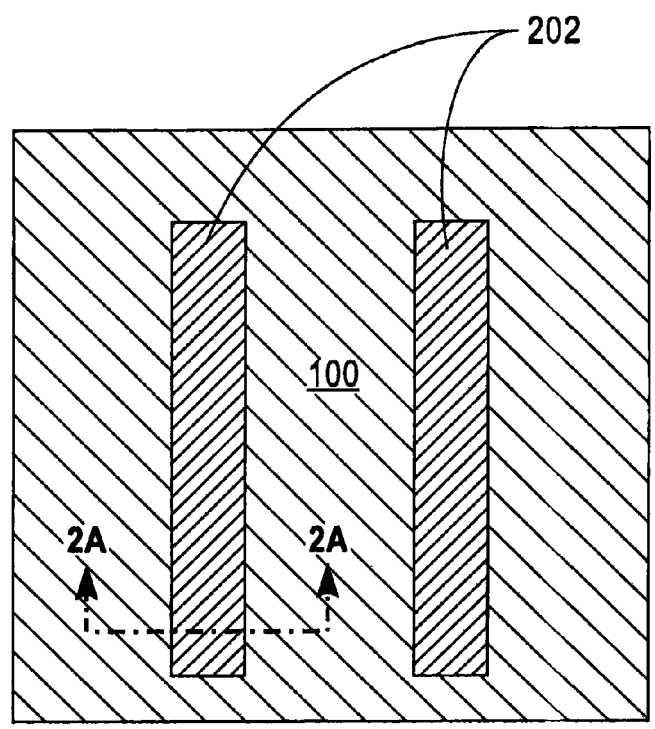

FIG. 2A illustrates a side view of the resultant structure following the deposition of a sacrificial layer 202 in the channel 102 (of FIG. 1). The sacrificial layer 202 may include for example, SiGe, Ge, materials. FIG. 2B illustrates a top-down view of the substrate 100 and sacrificial layers 202. Though the illustrated embodiment of FIG. 2B includes two sacrificial layer 202 regions, alternate embodiments may include any number of sacrificial layer 202 regions.

Figure 3:
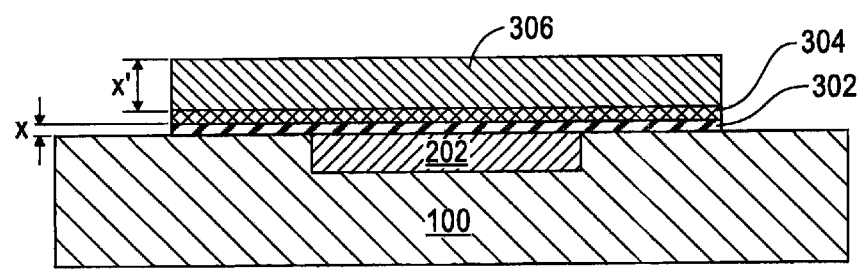

FIG. 3 illustrates a side view of the resultant structure following the deposition of a first dielectric layer 302 on the substrate 100 and the sacrificial layer 202; a graphene layer 304 on the first dielectric layer 302; and a second dielectric layer 306 on the graphene layer 304. The first dielectric layer 302 may include an insulating material such as, for example, $SiO_2$, $HfO_2$, $Si_3N_4$, $HfO_2$, $ZrO_2$, $Ta_2O_5$, $TiO_2$, or their mixtures, materials. The graphene layer 304 may include a graphene material such as, for example, a graphene tube The second dielectric layer 306 may include dielectric materials such as, for example, $HfO_2$ or $Si_3N_4$. In the illustrated embodiment, the thickness (x') of second dielectric layer 306 is greater than the thickness (x) of the first dielectric layer 302.

The graphene layer 304 may be formed by, for example, depositing a graphene material on the first dielectric layer 302, and a layer of thermal release tape (not shown) on the graphene material. A variety of thermal and mechanical processes are used to bond the graphene material to the first dielectric layer 302. The tape may be removed along with layers of the graphene material. The resultant structure includes a thin layer of graphene material (graphene layer 304) bonded to the first dielectric layer.

Figure 4:
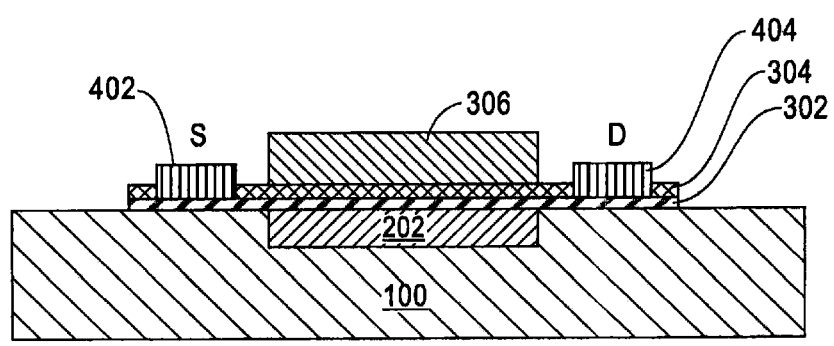

FIG. 4 illustrates the resultant structure following the removal of portions of the second dielectric layer 306 and portions of the graphene layer 304 that exposes portions of the graphene layer 304 and portions of the first dielectric layer 302. Source region (S) 402 and drain regions (D) 404 are formed on exposed portions of the first dielectric layer 302. The source and drain regions 402 and 404 are formed by, for example, direct metal deposition followed by thermal annealing to form an ohmic contact. The metal materials may include, for example, Ti, Au, W, Ag, or Ta.

Figure 5:
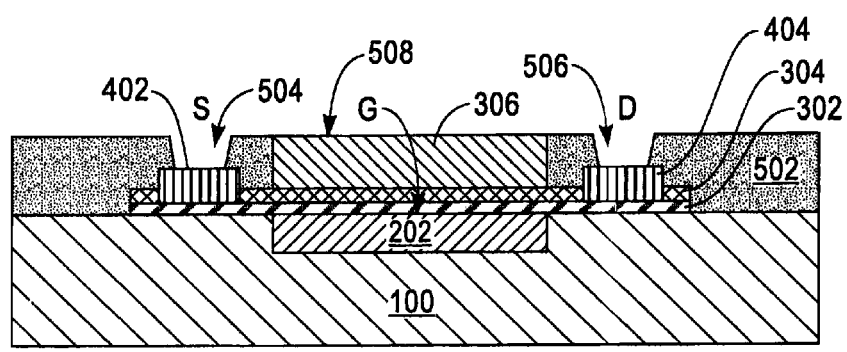

FIG. 5 illustrates the resultant structure following the deposition of a capping layer 502 on the exposed portions of the substrate 100, the sacrificial layer 202, the graphene layer 304, the source region 402, the drain region 404, and the second dielectric layer 306. In the illustrated embodiment, the thickness of the capping layer 502 has been reduced by, for example, a chemical mechanical polishing (CMP) or other suitable process, to expose the second dielectric layer 306. Cavities 504 and 506 may be formed by, for example, a lithographic etching process to expose the source and drain regions 402 and 404.

Figure 6A:
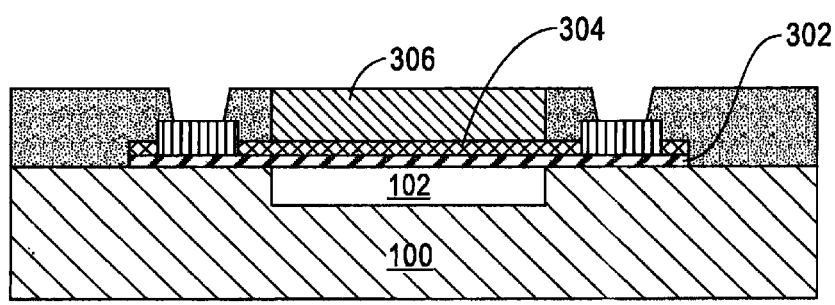
Figure 6B:
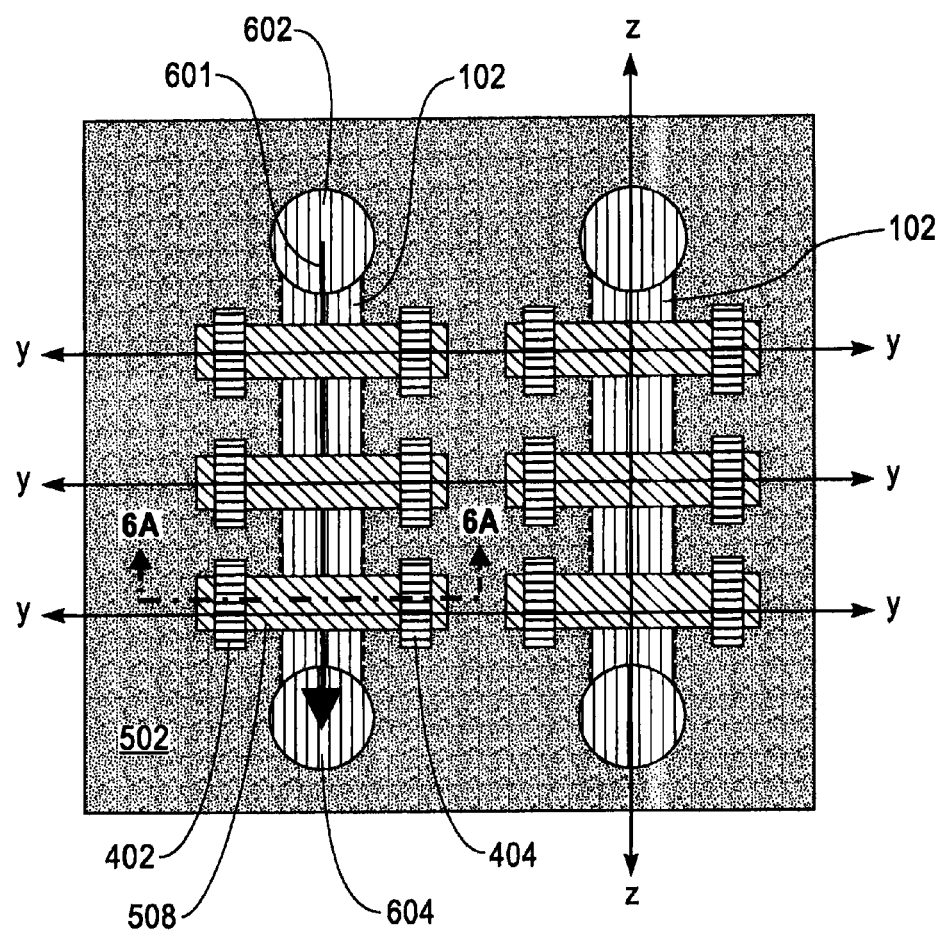

FIG. 6A illustrates the resultant structure following the removal of the sacrificial layer 202 (of FIG. 5) from the channel 102. FIG. 6B illustrates a top-down partially cutaway view of the resultant structure. Referring to FIG. 6B, the sacrificial layer 202 may be removed by removing portions of the capping layer 502 to form cavities 602 and 604 that expose opposing distal ends of the sacrificial layer 202. The cavities 602 and 604 may be formed by, for example, a lithographic etching process. Once the cavities 602 and 604 are formed, the sacrificial layer 202 may be removed by, for example, a selective isotropic etching process that removes the exposed sacrificial layer 202 material. The removal of the sacrificial layer 202 from the channel 102 forms a flow path indicated by the arrow 601. The flow path 601 enters the cavity 602 defined by the capping layer 502 and a first distal end of the channel 102. The flow path 601 runs under the first dielectric layer 302 (of FIG. 6A) and the capping layer 502 where the flow path 601 exits from the second cavity 604 defined by a second distal end of the channel 102 and the capping layer 502. The illustrated embodiment of FIG. 6B shows a number of devices arranged with longitudinal axis (y) orthogonal to the longitudinal axis (z) of the channel the channel 102.

In exemplary operation, a fluid having, for example single strand DNA flows through the flow path 601 (of FIG. 6B), and the resistance of the device is measured. Since different types of single strand DNA may change the measured resistance of the device (e.g., an increase or a decrease in resistance) the change in resistance of the device may indicate a type of DNA that is in the fluid. A fixed voltage bias is applied between the source and drain regions and the current is monitored. The resistance of the device is calculated by dividing the voltage by the measured current. When different types of DNA contact the gate dielectric layer 302, the transistor may be turned on or off. The resistance of the device reflects the change in state.

Referring to FIG. 6A, the relatively thin first dielectric layer 302, between the fluid in the flow path 601 (of FIG. 6B) and the graphene layer 304, improves the sensitivity of the device. Forming the first dielectric layer 302 on the substrate 100 allows (and sacrificial layer 202, prior to the removal of the sacrificial layer 202) the first dielectric layer 302 to be easily formed to a desired thickness. A relatively thin second dielectric layer 306 may be more difficult to precisely form on the graphene layer 304 due to the material properties of graphene. Forming the fluid flow path 601 such that the fluid contacts the thinner first dielectric layer 302, rather than the thicker second dielectric layer 306, maintains the desired sensitivity of the device.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one ore more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The diagrams depicted herein are just one example. There may be many variations to this diagram or the steps (or operations) described therein without departing from the spirit of the invention. For instance, the steps may be performed in a differing order or steps may be added, deleted or modified. All of these variations are considered a part of the claimed invention.

While the preferred embodiment to the invention had been described, it will be understood that those skilled in the art, both now and in the future, may make various improvements and enhancements which fall within the scope of the claims which follow. These claims should be construed to maintain the proper protection for the invention first described.

What is claimed is:

1. A method for forming a sensor, the method comprising:
   forming a channel in a substrate;
   forming a sacrificial layer in the channel;
   forming a gate dielectric layer on the substrate and the sacrificial layer, and a graphene layer on the gate dielectric layer;
   forming a source region on the gate dielectric layer, the source region also in contact with a first end of the graphene layer;
   forming a drain region on the gate dielectric layer, the drain region also in contact with a second end of the graphene layer;
   removing the sacrificial layer from the channel, wherein the channel comprises a physical opening formed in the substrate so as to define a gap between a bottom surface of the gate dielectric layer and a top surface of the substrate; and
   forming a first cavity in communication with a first end of the channel, and forming a second cavity in communication with a second end of the channel opposite the first end so as to define a fluid flow path comprising the first cavity, the channel, and the second cavity.

2. The method of claim 1, further comprising disposing a capping layer on the substrate, the graphene layer, the source region, the drain region and the sacrificial layer prior to removing the sacrificial layer from the channel, the first cavity and the second cavity being formed in the capping layer.

3. The method of claim 2, further comprising removing portions of the capping layer to expose the source region, the drain region, and a portion of the sacrificial layer prior to removing the sacrificial layer from the channel.

4. The method of claim 1, wherein the graphene layer includes a graphene tube.

5. The method of claim 1, wherein the sacrificial layer includes SiGe.

6. The method of claim 1, wherein a longitudinal axis of the channel is arranged orthogonally to a longitudinal axis that connects the source and drain regions.

7. The method of claim 1, wherein the substrate is a buried oxide (BOX) substrate.

8. A method for forming a sensor, the method comprising:
   forming a plurality of channels in a substrate, each of the plurality of channels having a longitudinal axis along a first direction;
   forming a sacrificial layer in the plurality of channels;
   for each of the plurality of channels, forming a plurality of gate dielectric layers on the substrate and the sacrificial layer, each of the gate dielectric layers having a longitudinal axis along a second direction orthogonal to the first direction;

forming a graphene layer on each gate dielectric layer;

for each gate dielectric layer, forming a source region on the gate dielectric layer, the source region also in contact with a first end of the graphene layer, and forming drain region on the gate dielectric layer, the drain region also in contact with a second end of the graphene layer;

forming a capping layer on the exposed substrate, graphene layer, source region and drain region;

removing the sacrificial layer from each channel, wherein each channel comprises a physical opening formed in the substrate so as to define a gap between a bottom surface of the gate dielectric layer and a top surface of the substrate; and for each channel, forming a first cavity in the capping layer communicative with the channel, and forming a second capping layer in the channel communicative with the channel so as to define a fluid flow path comprising the first cavity, the channel, and the second cavity.

9. The method of claim 8, wherein the graphene layer includes a graphene tube.

10. The method of claim 8, wherein the substrate is a buried oxide (BOX) substrate.

* * * * *